(12) United States Patent
Miyauchi et al.

(10) Patent No.: US 7,923,244 B2
(45) Date of Patent: Apr. 12, 2011

(54) ARTIFICIAL CARTILAGE TISSUE AND PRODUCTION METHOD THEREOF

(75) Inventors: Satoshi Miyauchi, Tokyo (JP); Tatsuya Miyazaki, Tokyo (JP); Satoshi Matsuzaka, Tokyo (JP)

(73) Assignee: PG Research Co., Ltd., Tokyo (JP)

( * ) Notice: Subject to any disclaimer, the term of this patent is extended or adjusted under 35 U.S.C. 154(b) by 761 days.

(21) Appl. No.: 11/699,400

(22) Filed: Jan. 30, 2007

(65) Prior Publication Data

US 2007/0184550 A1    Aug. 9, 2007

(51) Int. Cl.
  *C12N 5/071* (2010.01)
  *A61K 38/00* (2006.01)

(52) U.S. Cl. ..................... 435/366; 424/93.7

(58) Field of Classification Search .......... None
See application file for complete search history.

(56) References Cited

U.S. PATENT DOCUMENTS

| | | | |
|---|---|---|---|
| 5,326,357 A * | 7/1994 | Kandel | 623/23.72 |
| 5,786,217 A * | 7/1998 | Tubo et al. | 435/402 |
| 6,197,061 B1 | 3/2001 | Masuda et al. | |
| 6,451,060 B2 | 9/2002 | Masuda et al. | |
| 6,676,969 B2 * | 1/2004 | Geistlich et al. | 424/484 |
| 6,730,314 B2 * | 5/2004 | Jeschke et al. | 424/423 |
| 2002/0052044 A1 | 5/2002 | Jeschke et al. | |
| 2003/0153078 A1 * | 8/2003 | Libera et al. | 435/383 |

FOREIGN PATENT DOCUMENTS

| | | |
|---|---|---|
| JP | 2001-224678 | 8/2001 |
| JP | 2003-304866 | 10/2003 |
| WO | WO 00/17321 | 3/2000 |
| WO | WO 00/51527 | 9/2000 |
| WO | WO 01/60424 | 8/2001 |

OTHER PUBLICATIONS

Brittberg, M. et al., "Treatment of deep cartilage defects in the knee with autologous chondrocyte transplantation", N Engl J Med 331: 889-895 (Oct. 1994).*

Brittberg et al., "Treatment of Deep Cartilage Defects in the Knee with Autologous Chondrocyte Transplantation", The New English Journal of Medicine, vol. 331, No. 14, Oct. 6, 1994, pp. 889-895.

Rodriguez et al., "Characteristics of Cartilage Engineered from Human Pediatric Auricular Cartilage", Plastic and Reconstructive Surgery, vol. 103, No. 4, Apr. 1999, pp. 1111-1119.

Merrihew et al., "The Effect of Human Serum in the Production of Engineered Human Cartilage Constructs Using the Alginate-Recovered Chondrocyte Method", Paper No. 0821, $52^{nd}$ Annual Meeting of the Orthopaedic Research Society, 2006.

Masuda et al., "A novel two-step method for the formation of tissue-engineered cartilage by mature bovine chondrocytes: the alginate-recovered-chondrocyte (ARC) method", Journal of Orthopaedic Research, vol. 21, 2003, pp. 139-148.

Stoddart et al., "Generation of a scaffold free cartilage-like implant from a small amount of starting material", J. Cell. Mol. Med., vol. 10, No. 2, 2006, pp. 480-492.

Masuda et al., "Tissue-engineered Human Articular Cartilage produced from Knee Biopsy Specimens-Alginate-recovered-chondrocyte Method and Osteogenic Protein-1", Paper No. 6202, ICRS, 2002.

Matsuzaka et al., "Formation of Cartilaginous Tissue by the Alginate-Recovered-Chondrocyte Method and in vivo Transplantation to Full-Thickness Defects in Swine Articular Cartilage-Feasibility Study", Paper No. 0453, $48^{th}$ Annual Meeting of the Orthopaedic Research Society, 2002.

Chen et al., "Tissue Engineered Cartilage From Adult Human Chondrocytes: Biomechanical Properties and Function-Composition Relationships", Paper No. 945, $49^{th}$ Annual Meeting of the Orthopaedic Research Society, 2003.

Yanaga, Hiroko, et al., excerpt from "Microtia Operation Using Autologous Cultured Cartilage", The $48^{th}$ Annual Meeting of Japan Society of Plastic and Reconstructive Surgery, p. 196, No. 088, Mar. 18, 2005.

* cited by examiner

*Primary Examiner* — Anand U Desai (74) *Attorney, Agent, or Firm* — Young & Thompson (57) ABSTRACT

To obtain an artificial cartilage tissue having high strength and biocompatibility. There is provided an artificial cartilage tissue which is substantially free of heterologous protein and is substantially free of scaffold derived from non-cartilage-derived cells, but contains mammalian cartilage-derived cells and an extracellular matrix formed by the cartilage-derived cells, where: (1) the water retention per mg of tissue dry weight is 17.8 mg or less; (2) collagen of 5.57 µg or more per mg of tissue wet weight is contained; (3) proteoglycan of 9.22 µg or more per mg of tissue wet weight is contained.

8 Claims, 6 Drawing Sheets

ARTIFICIAL CARTILAGE TISSUE AND PRODUCTION METHOD THEREOF

BACKGROUND OF THE INVENTION

1. Field of the Invention

The present invention relates to an artificial cartilage tissue prepared using a tissue engineering technique, and a production method thereof.

2. Description of Related Art

Articular cartilage is an important tissue which covers the osteoepiphysis and is in charge of the smooth movement of joints. The articular cartilage has a structure in which chondrocytes are dispersed throughout a non-cellular tissue called an extracellular matrix (hereunder, referred to as "matrix") that is neither innervarated nor vascularized. Such a structure in which these cells are dispersed throughout a matrix, that is, the fact that a small number of cells exist per unit volume, and the absence of vasculature means a very poor ability of self-regeneration when an injury occurs.

When articular cartilage is damaged due to aging, trauma, or the like, smooth movement of the joint is interferred and an acute pain occurs in the joint. Although the cartilage itself is not innervated, since the articular capsule, which constitutes the joint, and the subchondral bone (bone under the cartilage) have sensory nerves, a feeling of pain is experienced.

If the cartilage tissue containing chondrocytes remains at the damaged site of the cartilage, there is a possibility of medicinal treatment by means of a growth factor, or the like. However, if the cartilage tissue itself is defective, there is no way to regenerate the cartilage other than implantation of external chondrocytes or cartilage tissue, or introduction of myeloid cells from the bone marrow underneath the cartilage so as to form a cartilage. The method of introducing myeloid cells from the bone marrow to form a cartilage is currently applied to traumatic cartilage damage. However, the regenerated cartilage is fibrocartilage which is poor in mechanical strength, and thus it is said that joint function lasts only for several years.

Moreover, it is difficult to introduce myeloid cells to form a cartilage at the cartilage defective site of osteoarthritis, which is a chronic degenerative disease of cartilage. The current state is that there is no way other than artificial joint replacement as a treatment method for the last stage of osteoarthritis. Artificial joint replacement is effective for relieving acute pains in the joint, but it is regarded as a "last resort" since the joint function is largely limited and the life span of the artificial joint is about 15 years (the interval between the bone of the patient and the artificial joint is loosened).

From the above reasons, treatment methods by means of implantation of chondrocytes or a cartilage tissue are drawing attention. As one of such methods, there is a means in which cartilage is collected from a dead body or the patient him/herself together with the bone underneath thereof (subchondral bone), and is grafted into the cartilage defective site. The method of using an osteochondral graft collected from a dead body involves problems of donor shortages and risks of infection. The method of using an osteochondral graft collected from a non weight-bearing region of the patient him/herself is called mosaicplasty, and recently, many clinical examples thereof have been reported. However, there are shortcomings in that the collection quantity is limited, and a large osteochondral defect wound remains at the collection site.

As another treatment method of implantating chondrocytes or cartilage tissue, there is a method of filling cultured chondrocytes or cultured cartilage tissue. This method is characterized in that a small amount of cartilage tissue is collected from the patient him/herself or someone else, and chondrocytes are isolated, then the chondrocytes are cultured in vitro until a target number of cells or a target shape is achieved. After a fixed period of culturing, the cultured chondrocytes or the cultured cartilage tissue (hereunder, a cartilage-repairing product) is implanted into the cartilage defective site. Such a technique is generally called a "regenerative medical technique" or "tissue engineering", and is under consideration not only for cartilage but also for various tissues and organs. Because of progress in control techniques of cell differentiation, recently it is shown that cultured chondrocytes can be prepared from embryo-stem cells or mesenchymal stem cells.

Various forms are being considered for implantation of artificial cartilage tissue prepared by culturing. As a leading example, there is a method in which chondrocytes isolated from a patient are monolayer cultured so as to increase the number of cells, which are then implanted into the cartilage defective site as a cell suspension (for example, refer to N. Engl. J. Med. 1994, 331, 889-895 (hereunder, called "reference 1")). In this method, in order to prevent the implant material from being scattered and lost, the implanted site is covered with a periosteal patch after the implantation.

As another method, a method is reported in which chondrocytes collected from a patient are inoculated in a scaffold (scaffolding material) of atelocollagen, and cultured, after which they are implanted as a paste-like collagen gel (for example, refer to Japanese Unexamined Patent Application, Publication No. 2001-224678 (hereunder, called "reference 2")).

Furthermore, in addition to the abovementioned atelocollagen, bioabsorbable synthetic polymers such as lactic acid/glycolic acid copolymer (PLGA) are also used as a scaffold of chondrocytes. Since these synthetic polymers have a high initial strength and may be given an arbitrary three dimensional shape, they are used not only for articular cartilages but also for preparing cultured auricular cartilages (for example, refer to Plast. Reconstr. Surg. 1999, 103, 1111-1119 (hereunder, called "reference 3")).

However, in the method of reference 1, if chondrocytes are monolayer cultured, inherent characteristics of the chondrocytes partially disappear (dedifferentiation), and therefore, requirements for the-implant material, such as "redifferentiation", "biosynthesis of the matrix", and "repair of the defective site" are increased, thus the time required for recovery is inevitably elongated. Moreover, a large number of the implanted cells are scattered and lost during that period, and thus many researchers are raising questions about the effect.

Moreover, in the method of reference 2, the implanted site is covered with a periosteal patch after implantation. This method minimizes dedifferentiation of chondrocytes, and thus better effects are expected compared to the monolayer cultured chondrocytes. However, a drawback is the necessity of the periosteal patch. Furthermore, because of the paste-like form, the strength is much weaker compared to the actual cartilage. This means that it takes a long time to form the actual cartilage, and it is difficult for it to be compatible with the cartilage of the weight-bearing region of the joint.

Furthermore, in the method of reference 3, when a synthetic polymer is used for articular cartilage, the engraftment rate after implantation is poor. The reason is that, since the cartilage is an avascular tissue without a bloodstream, it takes a long time for the synthetic polymer to disappear even if it is a bioabsorbable synthetic polymer, which may interfere with the fusion between the implant material and the surrounding tissue, and the alteration of the matrix composition into that of original articular cartilage during the time until the polymer disappears. In order to fundamentally solve the various problems involved in the usage of scaffolds, ideal is a cartilage-repairing product substantially free of scaffold.

On the other hand, serum or plasma used for culturing involves a very big problem in terms of the safety of the prepared artificial cartilage tissue. That is, many of the cultured chondrocytes or cultured cartilage tissues, reported so far, are prepared using fetal bovine serum (FBS). FBS shows a superior growth-stimulative effect and matrix synthesis-stimulative effect for chondrocytes, and thus is very effective for preparing artificial cartilage tissues, but has a risk of bovine spongiform encephalopathy (BSE) and a risk of immunogenicity due to a contaminant protein derived from FBS mixed in the artificial cartilage tissue. In the case of humans, such risks can be reduced by using an allogenic serum or plasma, however conversely, risks of human infections such as human immunodeficiency disease and hepatitis are increased. If no serum nor plasma is used, such risks can be completely excluded, but preparation of engraftable artificial cartilage tissues is very difficult in serum-free media or plasma-free media. Therefore, using cells derived from cartilage of the patient him/herself and an autologous serum or plasma is optimal in terms of ensuring safety, and is practical. However, it is difficult to prepare artificial cartilage tissues which are suturable with a superior engraftablility, that is, having a mechanical strength above a fixed level.

As described above, the fact is that artificial cartilage tissues have not been developed yet which, are substantially free of exogenous scaffold material and heterologous protein, have a superior mechanical strength, and can be expected to satisfactorily engraft. In terms of safety, an artificial cartilage tissue is preferable that is prepared using cells derived from an autologous cartilage and an autologous serum or plasma. Moreover, for implantation, an artificial cartilage tissue is desirable which can be sutured to a target site without using a periosteal patch, or the like.

BRIEF SUMMARY OF THE INVENTION

The present invention takes the above problems into consideration with the object of: establishing a preparation method of an artificial cartilage tissue which is substantially free of exogenous scaffolding material and heterologous contaminant protein, has a high safety, and has a fixed mechanical strength suturable with a suture thread; and providing an artificial cartilage tissue which has a fixed mechanical strength or composition showing a superior engraftablility, and a production method thereof.

In order to achieve the above object, the present inventors have earnestly studied the preparation method of an artificial cartilage tissue using an allogenic or autologous serum, and the composition, the mechanical strength, and the engraftability of the prepared artificial cartilage tissue. As a result, they have found to their surprise that culturing of cartilage-derived cells under conditions containing serum or plasma from a mammal over 6 months old, and with a growth factor belonging to the transforming growth factor-β (TGF-β) superfamily, provides an artificial cartilage tissue that has a low water retention, a high collagen content, a high proteoglycan content, and a biocompatibility with a superior strength, thus completing the present invention.

A first aspect of the present invention is an artificial cartilage tissue which is substantially free of heterologous protein and is substantially free of scaffold derived from non-cartilage-derived cells, but contains mammalian cartilage-derived cells and an extracellular matrix formed by the cartilage-derived cells, and satisfies the following (1), (2), or (3):

(1) the water retention per mg of tissue dry weight is 17.8 mg or less;
(2) collagen of 5.57 μg or more per mg of tissue wet weight is contained;
(3) proteoglycan of 9.22 μg or more per mg of tissue wet weight is contained.

The artificial cartilage tissue of the first aspect is preferably obtained by culturing cartilage-derived cells from a mammal under the presence of serum or plasma derived from a mammal of the same species.

In the first aspect, the serum or plasma is preferably derived from a mammal over 6 months old.

In the first aspect, the serum or plasma is preferably derived from the mammal which is the same individual.

In the first aspect, the mammal may be a human.

In the first aspect, the artificial cartilage tissue obtained as described above by culturing cartilage-derived cells from a mammal under the presence of serum or plasma derived from a mammal of the same species may be obtained by culturing in a medium containing a growth factor belonging to the transforming growth factor-β (TGF-β) superfamily.

In this case, the medium preferably contains 20 ng/mL or more of the growth factor belonging to the transforming growth factor-β (TGF-β) superfamily.

A second aspect of the present invention is a production method of artificial cartilage tissue comprising; isolating cartilage-derived cells from a mammal; and culturing the isolated cartilage-derived cells under the presence of serum or plasma derived from a mammal of the same species.

In the second aspect, the serum or plasma may be derived from a mammal over 6 months old. In the second aspect, the serum or plasma may be derived from the same individual.

In the second aspect, the mammal may be a human.

In the second aspect, if the serum or plasma is derived from a mammal over 6 months old, a step of culturing the cartilage-derived cells in a medium containing a growth factor belonging to the transforming growth factor-β (TGF-β) superfamily, is preferably included.

In this case, in the above invention, the medium preferably contains 20 ng/mL or more of the growth factor belonging to the transforming growth factor-β (TGF-β) superfamily.

The growth factor belonging to the transforming growth factor-β (TGF-β) superfamily may be a transforming growth factor-β1, ⊕2, or β3.

According to the present invention, an artificial cartilage tissue with superior strength and engraftablility can be obtained.

BRIEF DESCRIPTION OF THE SEVERAL VIEWS OF THE DRAWINGS

FIG. 1A and FIG. 1B are longitudinal cross-sections showing a culture dish having double silicon rings in the center used in Example 1 of a production method of an artificial cartilage tissue according to an embodiment of the present invention, wherein FIG. 1A shows a state where a cell suspension is inside silicon rings, and FIG. 1B shows a state where the silicon ring of the upper layer is taken out and the other silicon ring is soaked in a medium.

DETAILED DESCRIPTION OF THE INVENTION

Hereunder is a detailed description of an artificial cartilage tissue according to an embodiment of the present invention, and a production method thereof.

Firstly, the artificial cartilage tissue according to the present embodiment is described.

The artificial cartilage tissue according to the present embodiment contains mammalian cartilage-derived cells and an extracellular matrix formed by the cartilage-derived cells, and satisfies the following (1), (2), or (3):

(1) the water retention per mg of tissue dry weight is 17.8 mg or less;

(2) collagen of 5.57 μg or more per mg of tissue wet weight is contained;

(3) proteoglycan of 9.22 μg or more per mg of tissue wet weight is contained.

In this case, the mammal is not specifically limited. Examples thereof include apes, dogs, felines, equines, ovines, bovines, porcines, rabbits, murines, and humans, and more preferably, mammals other than bovines. Among them, humans are particularly preferable.

Moreover, the term cartilage-derived cells refers to cells present in cartilage, which are preferably cells obtained by decomposing and removing an extracellular matrix from cartilage collected from a living body.

The most abundant constituent in artificial cartilage tissue is water. Other main constituents other than water are an extracellular matrix and chondrocytes. Although the water content is usually expressed as weight % per unit wet weight, it is expressed as water retention in the present invention. The water retention means the water quantity retained in a cartilage per unit dry weight, and reflects variations more sensitively compared to the water content (weight % per cartilage wet weight).

The main constituents of the extracellular matrix in artificial cartilage tissue are collagen and proteoglycan. The collagen is mainly type II, and a small amount of other collagens such as type I, type IX, and type XI are contained. Moreover, a large portion of the proteoglycan is composed of aggrecan.

The water retention of the artificial cartilage tissue in the present embodiment is 17.8 mg/mg of dry weight or less, preferably 16 mg/mg of dry weight or less, and most preferably 14 mg/mg of dry weight or less. The reason is that the artificial cartilage tissue according to the present embodiment having such a water retention is superior in mechanical strength, is suturable and can be expected to have a high engraftment rate.

The collagen content of the artificial cartilage tissue in the present embodiment is 5.57 μg/mg of wet weight or more, preferably 11.1 μg/mg of wet weight or more, and most preferably 12.4 μg/mg of wet weight or more. The reason is that the artificial cartilage tissue according to the present embodiment having such a collagen content is superior in mechanical strength, is suturable, and can be expected to have a high engraftment rate.

The proteoglycan content of the artificial cartilage tissue in the present embodiment is 9.22 μg/mg of wet weight or more, preferably 12.2 μg/mg of wet weight or more, and most preferably 13.4 μg/mg of wet weight or more. The reason is that the artificial cartilage tissue according to the present embodiment having such a proteoglycan content can be expected to have a high engraftment rate.

Although the artificial cartilage tissue according to the present embodiment has a preferable amount of the above-mentioned water retention, collagen content, and proteoglycan content, it is most preferable, if all of them are within the preferable range.

Moreover, the artificial cartilage tissue according to the present embodiment is substantially free of scaffold derived from non-cartilage cells. That is, a cartilage tissue generally has a high elasticity and a high fatigue resistance. Consequently, these properties are essential in the artificial cartilage tissue. Generally, in order to ensure these properties, an exogenous scaffold is used for an artificial cartilage tissue in some cases. However, even without having such an exogenous scaffold, the artificial cartilage tissue according to the present embodiment has high elasticity and fatigue resistance. Here, "substantially free of" includes "nothing is intentionally added to".

Such an artificial cartilage tissue according to the present embodiment is obtained by culturing cartilage-derived cells from a mammal under the presence of serum or plasma derived from a mammal of the same species.

Here, it is possible to use any serum or plasma as long as they are collected from an animal of the same species as the mammal from which the cartilage-derived cells are collected. Particularly among them, the serum or plasma is preferably derived from a mammal over 6 months old, or collected from the same individual.

Next is a description of a production method of an artificial cartilage tissue according to the present embodiment.

In the production method of an artificial cartilage tissue according to the present embodiment, cartilage-derived cells are isolated from a mammal, and the isolated cartilage-derived cells are cultured to produce cartilage tissue. The cartilage-derived cells are cultured under the presence of serum or plasma derived from a mammal of the same species, or the same individual.

Here, the term serum means a light yellow liquid obtained as a supernatant as a result of coagulation of blood collected from an animal artery or vein which is left in an appropriate container, and removal of the coagulum (called a blood clot) by means of centrifugation or the like. Hematocytes and several types of blood coagulation factors are removed from the blood constituent. The term plasma in the present invention means the fraction of blood collected from an animal artery or vein from which hematocytes have been removed, and is normally the light yellow liquid obtained as a supernatant by centrifugation of blood added with an anticoagulant.

More specifically, the artificial cartilage tissue according to the present embodiment can be prepared by, for example, the following method.

(1) Isolation of Cells from Cartilage Tissue

In the present step, cartilage is aseptically collected, the collected cartilage is then pretreated using a proteolytic enzyme in a medium free of serum and plasma (hereunder, referred to as "serums"), and thereafter, the cartilage is treated in a medium containing a collagenase and serums, to isolate cells.

Here, the term proteolytic enzyme may be used as long as it is an enzyme such as papain, trypsin, protease, and pronase that are known to decompose proteins. The dosage and the treatment time of such an enzyme are preferably a concentration and a treatment time sufficient to obtain chondrocytes from the collected cartilage tissue. Such concentration and treatment time can be readily and appropriately adjusted by a person skilled in the art.

(2) Monolayer Culture of Cells

In the present step, the isolated chondrocytes of (1) are cultured in a medium containing a fibroblast growth factor, an insulin-like growth factor, and serums.

Here, the medium is not specifically limited as long as it is a medium used for culturing chondrocytes. Preferable examples thereof include Dulbecco's Modified Eagle's Medium and Ham's F12 Medium. Most preferable is a medium containing these media at a ratio of 1:1.

The fibroblast growth factor used in the present step is particularly preferably a basic fibroblast growth factor. Examples of the application concentration include 1 ng/mL to 500 ng/mL, and particularly preferably 10 to 300 ng/mL.

The insulin-like growth factor used in the present step is not specifically limited, but is preferably an insulin-like growth factor I. Examples of the application concentration include 1 ng/mL to 1000 ng/mL, and preferably 50 to 500 ng/mL.

The serums used in the present step are derived from a mammal of the same species or the individual mammal, from which the cartilage-derived cells are collected. The dosage of such serums in the medium is, for example, 3 to 30%, and preferably about 5 to 20%.

The culturing in the present step is continued until the number of cells is increased to at least $5 \times 10^6$ or more.

Other substances (such as an antibiotic) may be contained in the medium.

(3) Three Dimensional Culture

In the present step, the chondrocytes obtained in the previous step are detached from the culture dish, and dispersed, the cells are then embedded in a sodium alginate gel, and the cells in the gel are cultured in a medium.

As a substance used for detachment and dispersing the chondrocytes, a proteolytic enzyme such as collagenase, protease, and pronase can be used. The dosage and the treatment time of these enzymes can be readily and appropriately selected by a person skilled in the art.

The medium in the present step is the same medium as in step (2). Such a medium contains an insulin-like growth factor I and serums similarly to in step (2).

In the present step, cells are embedded in a sodium alginate gel. Such an embedding is performed, for example, such that separated cells are dispersed in a physiological saline solution containing sodium alginate, and this physiological saline solution is added dropwise to a solution containing calcium ions (such as calcium chloride) to coagulate the sodium alginate so as to form a gel.

In such a condition, the cells are cultured for 10 to 20 days, and preferably 12 to 16 days.

(4) Formation of Artificial Cartilage Tissue

The alginate gel is dissolved by a chelating agent, and the chondrocytes are collected. Then, the chondrocytes suspended in the medium are transferred to a culture container of a desired shape, and cultured therein. A growth factor belonging to the transforming growth factor-β (TGF-β) superfamily, an insulin-like growth factor, and autologous or allogenic serums, are added to the medium for culturing.

Here, examples of the chelating agent include ethylenediaminetetraacetic acid and citric acid. The type of such a chelating agent is not limited as long as it does not negatively affect the cultured cells. The dosage and the concentration of such a chelating agent can be appropriately adjusted so as to dissolve the alginate gel, by a person skilled in the art.

Moreover, the growth factor belonging to the transforming growth factor-β superfamily means a group of peptide factors having a similar structure to that of the transforming growth factor-β, with two characteristics: the factor is produced as a precursor composed of about 200 to 400 amino acids, then a portion composed of 110,to 140 amino acids at the C terminal side is fragmented, and this portion becomes an active form; and seven cysteine residues are reserved in the peptide at the C terminal side of the active form. Specifically, it means types of growth factors such as transforming growth factor-β1, β2, and β3, activin-A, B, AB, C, and E, inhibin-A and B, follistatin, bone morphogenetic protein-2, 3, 4, 5, 6, 7, and 8, and growth and differentiation factor-5, 6, 7, 8, 9, and 11.

After the alginate gel is dissolved, the chondrocytes are collected by means of centrifugation, filtration, or the like. The cells obtained in this manner are cultured in a medium containing a growth factor belonging to the transforming growth factor-β superfamily (preferably a transforming growth factor-β1 or β2), and an insulin-like growth factor (preferably an insulin-like growth factor I). The medium preferably contains 5 ng/mL to 200 ng/mL, and in particular, 10 ng/mL to 50 ng/mL of the transforming growth factor-β. Moreover, the preferable concentration of the insulin-like growth factor in the medium is, for example, 1 ng/mL to 1000 ng/mL, and in particular, 50 ng/mL to 500 ng/mL.

The medium is similar to the medium in step (2), and an antibiotic may be appropriately added thereto.

The serums used in the present step are similar to the serums described in step (2), and are derived from a mammal of the same species or the same individual, from which the cartilage-derived cells are collected. The dosage of such serums in the medium is, for example, 1 to 40%, and preferably about 5 to 20%.

EXAMPLES

Hereunder is a more specific description of the artificial cartilage tissue according to the present embodiment and the production method thereof.

Measurement Example 1

Measurement of Mechanical Strength of Artificial Cartilage Tissue (1) Tear Strength Test An artificial cartilage tissue prepared to a diameter of 5 mm and a thickness of 1 mm was used as the sample. Two 6-0 nylon suture threads (Matsuda Ika Kogyo, Co., Ltd.) of about 10 cm were passed through the center of the sample, and the opposite ends of the respective suture threads were tied up in a ring form while attention was given so as to not cross the suture threads over each other. Next, one suture thread was fixed. The other suture thread was fixed to a digital force gauge (Nidec-Shimpo Corporation) and pulled at a speed of 4.8 mm/min or 6 mm/min. The load was recorded over time, and the load (unit is N) at which the artificial cartilage tissue was torn was recorded. The room temperature at the time of measurement was 25° C. In the implantation, since a 6-0 nylon thread was used for suture the artificial cartilage tissue to the surrounding cartilage, the tear strength with respect to the 6-0 nylon thread was measured.

Measurement Example 2

Biochemical Properties of Artificial Cartilage Tissue (1) Water Retention

The sample was taken out from the medium, and rotated 2 or 3 times on a KimTowel (Nippon Paper Crecia Co., Ltd.) so as to remove the adhered medium. The weight of the sample was measured, and this was referred to as the wet weight. Next, the sample was frozen and lyophilized using a freeze dryer (Tokyo Rikakikai Co., Ltd.). The weight of the lyophilized sample was measured, which was referred to as the dry weight. From the wet weight and the dry weight, the water retention per mg of dry weight was calculated using the following equation.

$$\text{water retention (mg H}_2\text{O/mg of dry weight)}=(\text{wet weight (mg)}-\text{dry weight (mg)})/\text{dry weight (mg)}$$

(2) Pretreatment of Sample 1 mL of 20 mmol/L HEPES buffer (pH 7.5) containing 1 mg/mL of pronase (Calbiochem Co.) was added to the sample whose dry weight had been measured, and the mixture was sealed to effect digestion at 60° C. for 3 hours. The obtained digestion liquid was used as a sample for analyzing the DNA content, the collagen content, and the proteoglycan content.

(3) DNA Content

According to the method of Kim Y-J et al. (Anal. Biochem., 1988, 174, 168-176), the DNA content was measured using a fluorescent dye (Hoechst 33258) of Hoechst AG with bovine thymus-derived DNA (Sigma Corporation) as the reference.

50 µL of the pretreated sample and 50 µL of the reference sample with a known concentration were placed in a 96 well black plate (Cat No. 437111, Nunc Co., Ltd.), and the same amount of 100 mM Tris-EDTA-NaCl buffer (pH 7.4) was added thereto. 20 mmol/L HEPES buffer (pH 7.5) containing the pronase used in the pretreatment was used as the negative control sample. Next, 100 µL of 5 µg/mL Hoechst 33258 solution dissolved in the same buffer was added to each sample, which was shaken in a shaker for 1 minute. Then, the measurement was performed using a fluorescence plate reader (Twinkle LB970, Berthold Technologies) with an excitation wavelength of 360 nm and a fluorescence wavelength of 460 nm. A calibration curve was formed based on the fluorescence intensity of the reference sample, and the DNA content in each sample was calculated from the calibration curve.

(4) Collagen Content

According the method of Woessner J F. Jr (Arch. Biochem. Biophys., 1961, 93, 440-447), the collagen content was calculated by measuring the hydroxyproline in the hydrolyzed sample.

100 µL of the pretreated sample was placed in a glass vial container (08-CPV, Chromacol Ltd.), the same amount of hydrochloric acid (Wako Pure Chemical Industries, Ltd.) was added thereto, and following sealing with an aluminum cap with tetrafluoroethylene septum (8-AC-TST1, Chromacol Ltd.), hydrolysis was effected at 120° C. for 16 hours. 20 mmol/L HEPES buffer (pH 7.5) containing the pronase used in the pretreatment was used as the negative control sample. Moreover, a porcine type II collagen solution (Chondrex, Inc.) with a known concentration was used as the reference sample.

A fixed amount of the hydrolyzed sample was separately taken and was 5-fold diluted by adding distilled water thereto. In total, it ended up as a 10 fold-dilution compared to the pretreated sample. 50 µL of the diluted sample was placed in a 0.8 mL deep well plate (AB-0765, ABgene House Co., Ltd.), then dried under reduced pressure to harden in a vacuum desiccator having coexisting sodium hydroxide. Distilled water was added to the dried sample, whose absorbance was measured at 557 nm after coloring according to the method of Woessner J F. Jr. A calibration curve was formed based on the absorbance of the reference sample, and the collagen content in each sample was calculated from the calibration curve.

(5) Proteoglycan Content

According the method of Bitter, T. et al. (Anal. Biochem., 1962, 4, 330-334), the proteoglycan content was calculated by measuring the total amount of uronic acid in the pretreated sample. Proteoglycan purified from a porcine articular cartilage was used as the reference sample. 20 µL of the pretreated sample and 130 µL of distilled water were placed in a glass test tube and chilled in ice. 1 mL of sulfuric acid (Wako Pure Chemical Industries, Ltd.) solution containing 25 mM sodium tetraborate (Wako Pure Chemical Industries, Ltd.) was added thereto. The mixture was sufficiently stirred, and then heated in a boiling water bath for 10 minutes. After chilling in ice, 35 µL of ethanol (Wako Pure Chemical Industries, Ltd.) solution containing 1.25 mg/mL carbazole (Wako Pure Chemical Industries, Ltd.) was added thereto, and the mixture was stirred. After heating in a boiling water bath for 15 minutes, the mixture was chilled in ice, and the absorbance was measured at 530 nm. A calibration curve was formed based on the absorbance of the reference sample, and the proteoglycan content in each sample was calculated from the calibration curve.

Example 1

Preparation of Artificial Cartilage Tissue Using Cells Derived from Porcine Articular Cartilage and its Mechanical and Biochemical Properties 1. Purpose The purpose is to prepare an artificial cartilage tissue using cells derived from a porcine articular cartilage, to select the main constituents that reflect the mechanical strength, and to understand the contents of the main constituents having the suturable mechanical strength in the artificial cartilage tissue.

2. Cell Isolation

A hind-leg of an approximately one-year old LWD porcine was purchased from Shimoda Chikusan Limited. The knee joint was opened, and femur articular cartilage was aseptically collected. Hereinafter, according to a partially modified method of Mok S. S. et al. (J. Biol. Chem., 1994, 269, 33021-33027), cells derived from the articular cartilage (hereunder, referred to as chondrocytes) were isolated.

The collected cartilage was put in a DMEM/F-12 medium (medium containing Dulbecco's Modified Eagle's Medium and Ham's F12 Medium at a ratio of 1:1, Invitrogen Corporation) containing 0.2% pronase (Calbiochem Co.) and 50 μg/mL gentamycin (Invitrogen Corporation). The mixture was treated by stirring using a stirrer under the presence of 5% $CO_2$ at 37° C. for 1 hour. Following the removal of the medium, a medium containing 0.025% collagenase-P (Roche) and 5% porcine serum (Invitrogen Corporation) was added to the residue, and this was digested under the presence of 5% $CO_2$ at 37° C. for 16 hours. After digestion, the cells were washed and collected by a 70 μm cell strainer (Becton, Dickinson and Company.). Then, the number of cells was measured using a hematocytometer.

3. Monolayer Culture

The Monolayer culture was performed as follows according to a partially modified method of Trippel S. B. et al. (J. Bone and Joint Surg., 1993, 75, 177-189). The isolated chondrocytes were put in a DMEM/F-12 medium containing 10 ng/mL basic fibroblast growth factor (bFGF, Kaken Pharmaceutical Co., Ltd.), 100 ng/mL insulin-like growth factor I(IGF-I, Fujisawa Pharmaceutical Co., Ltd.), 10% porcine serum, 25 μg/mL L-ascorbic acid (Sigma Corporation), and 10 μg/mL gentamycin, so that the number of cells was adjusted to $2 \times 10^6/30$ mL, and the total amount was inoculated in a culture dish (Becton, Dickinson and Company.) having a diameter of 15 cm.

Then, the cells were cultured under the presence of 5% $CO_2$ at 37° C. for 6 days, so as to keep the necessary number of cells ($9.4 \times 10^7$) for the next step. The medium was replaced every 2 to 3 days.

4. Three Dimensional Culture

A DMEM/F-12 medium containing 0.2% pronase and 10 μg/mL gentamycin was added to a culture dish containing the monolayer cultured chondrocytes, which was treated under the presence of 5% $CO_2$ at 37° C. for 15 minutes. The medium containing detached cells was collected and centrifuged at 300×g. The supernatant was disposed. The residue was digested by adding a medium containing 0.025% collagenase-P under the presence of 5% $CO_2$ at 37° C. for 1 hour. The dispersed cells were suspended in a physiological saline solution containing 1.2% sodium alginate (ISP) with a density of $2 \times 10^6$/mL. Hereinafter, according to a partially modified method of Flechtenmacher J. et al. (Arthritis Rheum., 1996, 39, 1896-1904), three dimensional culture was performed using an alginate gel.

The sodium alginate solution having the suspended cells was placed in a 50 mL disposable syringe (Terumo Corporation), and a 22G injection needle (Terumo Corporation) was equipped therein. The plunger of the syringe was pushed in, and the content liquid was added dropwise to a 102 mmol/L $CaCl_2$ (Sigma Corporation) solution. This allowed the alginic acid to be gelled in bead form while containing the cells. The diameter of the alginate beads was about 2 mm, and each bead contained about $2 \times 10^4$ chondrocytes. In 10 minutes after the dropwise addition, the beads were washed with a physiological saline solution three times. Then, the cells were cultured in a DMEM/F-12 medium containing 100 ng/mL IGF-I, 5% or 10% porcine serum, 25 μg/mL L-ascorbic acid, and 10 μg/mL gentamycin under the presence of 5% $CO_2$ at 37° C. for 14 days. The liquid volume of the medium was 45 mL per 1000 beads, and a culture dish having a diameter of 15 cm was used. The medium was replaced every second day. This three dimensional culture allowed the chondrocytes to produce proteoglycan and type II collagen serving as the cartilage matrix constituent, in the surroundings thereof.

5. Formation of Artificial Cartilage Tissue

After 14 days of three dimensional culture, according to the method of Mok S. S. et al. (J. Biol. Chem., 1994, 269, 33021-33027), 55 mmol/L sodium citrate buffer (pH 6.8) containing 0.15 mol/L sodium chloride was added at a 5-to-1 volume ratio to the alginate beads, and the mixture was stirred and left at room temperature for 15 minutes. The alginic acid gelled by Ca ions was dissolved by citric acid. The obtained suspension was centrifuged at 300×g at 4° C. for 5 minutes, and then a physiological saline solution was added to the precipitate, which was stirred and centrifuged in the same manner. This process was repeated once more using a physiological saline solution, and was repeated once using a medium described below. The chondrocytes having cartilage matrix were collected as a precipitate.

Figure 1A:
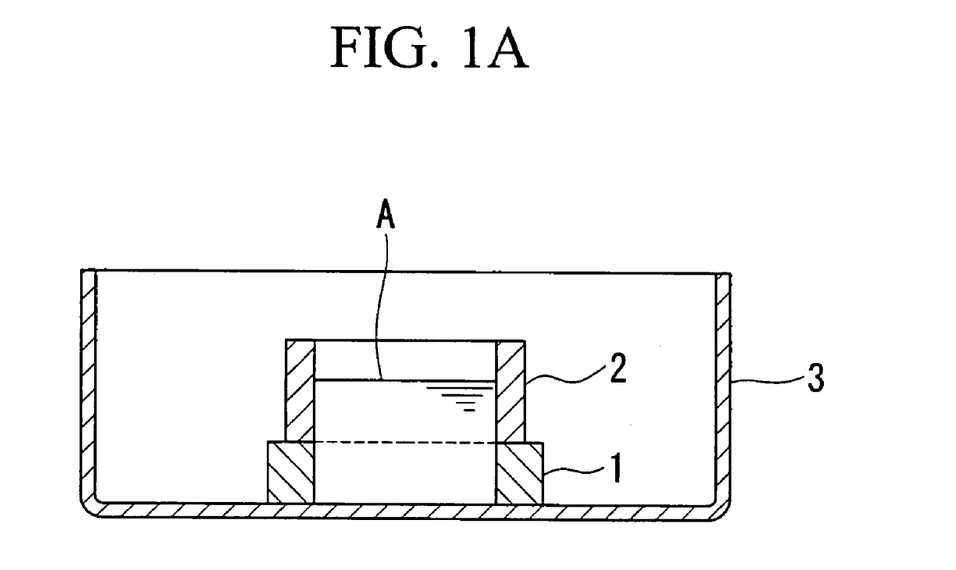
Figure 1B:
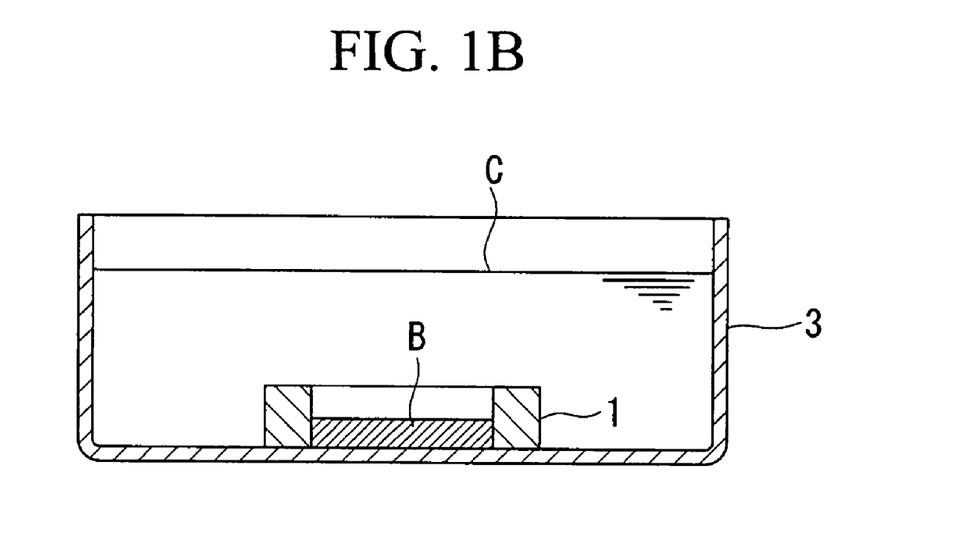

About 250 μL of the precipitate containing chondrocytes was suspended in a DMEM/F-12 medium containing 20 ng/mL transforming growth factor β1 (TGF-β1, R&D Systems), 100 ng/mL IGF-I, 5% or 10% porcine serum, 25 μg/mL L-ascorbic acid, and 10 μg/mL gentamycin. Next, as shown in FIG. 1A and FIG. 1B, a 6-well culture dish (Becton, Dickinson and Company.) 3 was prepared wherein a first layer (bottom layer) silicon ring 1 having an inner diameter of 15 mm, an outer diameter of 25 mm, and a height of 3 mm, and a second layer (top layer) silicon ring 2 having an inner diameter of 15 mm, an outer diameter of 19 mm, and a height of 10 mm were pressed onto the center. The silicon ring 2 of the top layer could be taken out. The cell suspension A was gently put in the silicon rings 1 and 2, and left under the presence of 5% $CO_2$ at 37° C. for 16 hours, to allow precipitation of cells B with a cartilage matrix in the silicon ring 1.

In this condition, the silicon ring 2 of the top layer was taken out. Next, 10 mL of a medium C used for suspending the cells B was added to soak the cells B precipitated in the silicon ring 1 of the bottom layer. In this condition, the cells were cultured under the presence of 5% $CO_2$ at 37° C. This culturing allowed the cartilage matrix of the respective cells B to be fused with each other, and an artificial cartilage tissue having a mechanical strength above a fixed level was able to be prepared. The basic culture period was set at 14 days. However, changing the culture period enabled the preparation of artificial cartilage tissues having various mechanical strengths.

The diameter of the artificial cartilage tissue prepared according to the above method was about 14 mm and the thickness thereof was about 1 mm. 148 samples were selected. Disc-shaped samples having a diameter of 5 mm were punched out, and the tear strength was measured. Moreover, after the disc-shaped samples were punched out, the remaining samples were used to measure the water retention, the collagen content, and the proteoglycan content serving as the main constituents of the artificial cartilage tissue.

6. Correlation of Tear Strength and Content of Main Constituents

The results of correlation analysis between tear strength and water retention, collagen content, or proteoglycan content are shown in Table 1.

TABLE 1

| Main Constituent Content | | Correlation with Breaking Load |
|---|---|---|
| Water Retention | | r = −0.587 (p < 0.01) |
| Collagen Content | per wet weight | r = 0.749 (p < 0.01) |
| | per dry weight | r = 0.679 (p < 0.01) |
| Proteoglycan Content | per wet weight | r = 0.335 (p < 0.01) |
| | per dry weight | r = −0.088 (NS) | r: Correlation Coefficient
NS: Not Significant

The most correlated measurement item with tear strength was collagen content per wet weight, followed by collagen content per dry weight, and water retention in this order. Although the proteoglycan content per wet weight was also significantly correlated, its correlation coefficient was low compared to the above measurement items, and the proteoglycan content per dry weight was not correlated.

Figure 2:
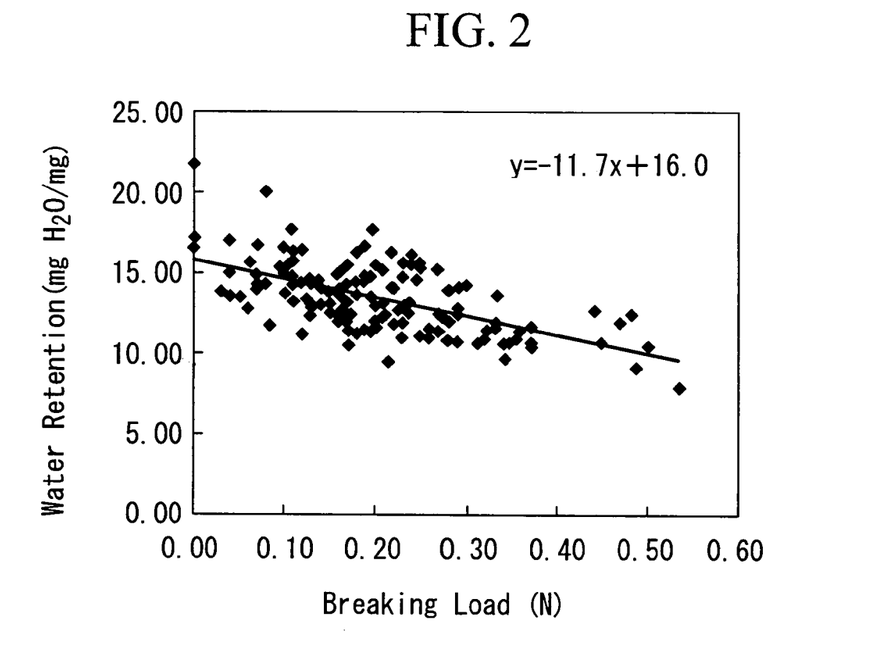
FIG. 2 is a graph showing the relation between water retention and tear strength in Example 1 of porcine artificial cartilage tissue according to an embodiment of the present invention.
Figure 3:
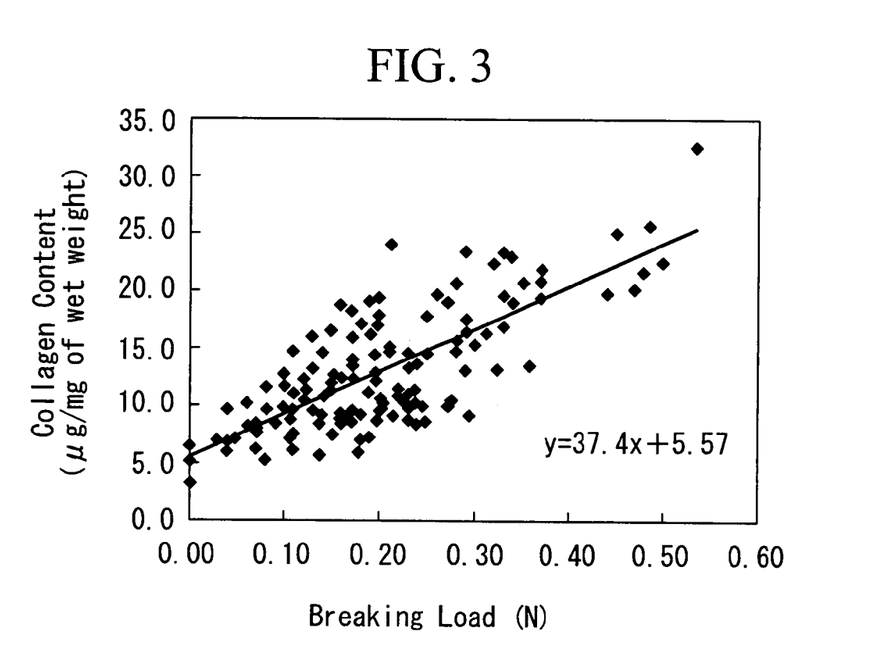
FIG. 3 is a graph showing the relation between collagen content and tear strength in Example 1 of porcine artificial cartilage tissue according to an embodiment of the present invention.
Figure 4:
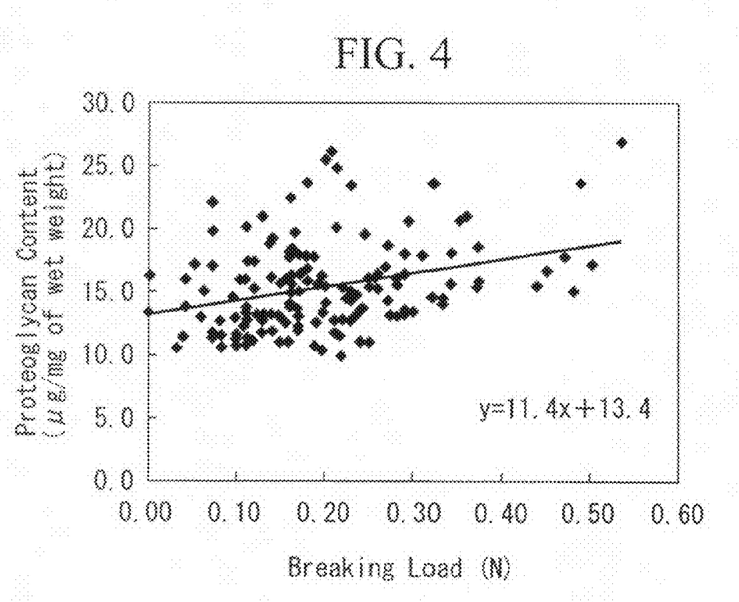
FIG. 4 is a graph showing the relation between proteoglycan content and tear strength in Example 1 of porcine artificial cartilage tissue according to an embodiment of the present invention.

Moreover, FIG. 2 shows the correlation between water retention and tear strength, FIG. 3 shows the correlation between collagen content per wet weight and tear strength, and FIG. 4 shows the correlation between proteoglycan content per wet weight and tear strength. According to these figures, the correlation equation between water retention and tear strength (breaking load) is: water retention (mg $H_2O$/mg of dry weight)≈−11.7×breaking load+16.0, the correlation equation between collagen content and tear strength is: collagen content (μg/mg of wet weight)≈37.4×breaking load+ 5.57, and the correlation equation between proteoglycan content and tear strength is: proteoglycan content (μg/mg of wet weight)≈11.4×breaking load+13.4.

The water retention of artificial cartilage tissue having a tear strength more than 0, that is, a suturable strength with a 6-0 nylon thread, was about 16.0 mg $H_2O$/mg of dry weight or less, the collagen content thereof was about 5.57 μg/mg of wet weight or more, and the proteoglycan content was about 13.4 μg/mg of wet weight or more.

7. Conclusion

The porcine artificial cartilage tissue having a suturable strength had at least a water retention of about 16.0 mg $H_2O$/mg of dry weight or less, a collagen content of about 5.57 μg/mg of wet weight or more, or a proteoglycan content of about 13.4 μg/mg of wet weight or more.

Example 2

Implantation of Artificial Cartilage Tissue Prepared by Using Cells Derived from Porcine Articular Cartilage into Pig Knee Joint 1. Purpose The purpose is to discuss the safety of an artificial cartilage tissue prepared by using serum derived from a heterologous animal or an animal of the same species, and to understand the range of water retention and collagen content required for engraftment.

2. Artificial Cartilage Tissue

According to the method described in Example 1, six artificial cartilage tissues were prepared by using cells derived from porcine articular cartilage. However, two samples were prepared by using fetal bovine serum (FBS) instead of porcine serum. The diameter of the prepared artificial cartilage tissue was about 14 mm and the thickness thereof was about 1 mm. These samples were punched out in a disc-shape having a diameter of 8 mm, and the obtained samples were used for implantation. After the disc-shaped samples were punched out, the remaining samples were used to measure the water retention and the collagen content.

3. Implantation into Experimental Animal

Four approximately six month old LWD female pigs were used. The body weight at the time of implantation was 83.5 to 93.0 kg. As a preanesthetic medication, 0.05 mg/kg of atropine sulfate (Tanabe Seiyaku Co., Ltd.) was intramuscularly administrated. Then, 2 mg/kg of xylazine hydrochloride (Bayer AG) and 20 mg/kg of ketamine hydrochloride (Sankyo Co., Ltd.) were intramuscularly administrated to effect anesthesia. Then, thiamylal sodium (Mitsubishi Pharma Corporation.) was appropriately administered into the veins to retain the anesthesia.

The vicinity of the knee of the right hind leg was shaved off, and sufficiently disinfected with Isodine (Meiji Seika Kaisha, Ltd.) Next, the skin, the muscular layer, and the articular capsule were incised to expose the medial condyle of the femur. Two cartilage full-thickness defects having a diameter of 8 mm were formed in the weight-bearing region of the articular surface, and the porcine artificial cartilage tissue prepared in Example 1 was inserted into the defects. Next, using a 6-0 nylon suture thread (Matsuda Ika Kogyo, Co., Ltd.), the artificial cartilage tissue was sutured to the cartilage around the implanted site at 4 points. Inside of the joint cavity was sufficiently washed with a physiological saline solution (Otsuka Pharmaceutical Co., Ltd.), and then the articular capsule, the muscular layer, and the skin were sequentially sutured. After the implantation operation, the pigs were kept warm until they woke up from anesthesia. On the day of the implantation operation and everyday for 7 days after the operation, 0.05 mg/kg of dihydrostreptomycin sulfate (Meiji Seika Kaisha, Ltd.) was intramuscularly administrated.

4. Anatomy and Observation of Implanted Tissue

Figure 5:
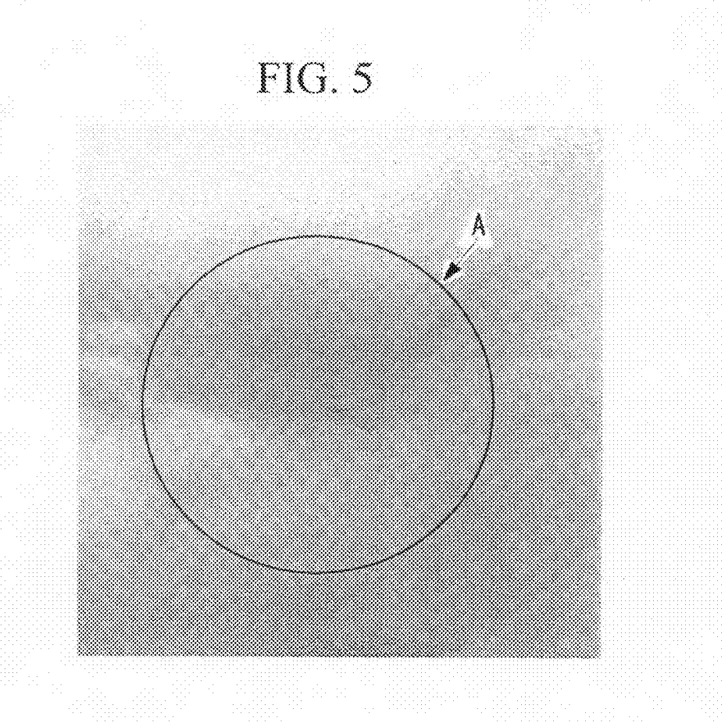
FIG. 5 shows a photograph of an engraftment condition of artificial cartilage tissue prepared by using a porcine serum in Example 2 of artificial cartilage tissue according to an embodiment of the present invention.

On the 13th week after implantation of the artificial cartilage tissue, the pigs were anesthetized with pentobarbital (Dainippon Pharmaceutical Company Limited.), and then allowed to bleed to death from the carotid artery. The condyle of femur of the right hind leg was separated, and the condition of the implanted site was macroscopically observed. As a result, engraftment was ensured for all artificial cartilage tissues prepared using porcine serum. Regarding the engraftment condition, no big difference was recognized between the respective samples. A photograph of a representative example is shown in FIG. 5. In the drawing, the symbol A shows the implanted site.

Figure 6:
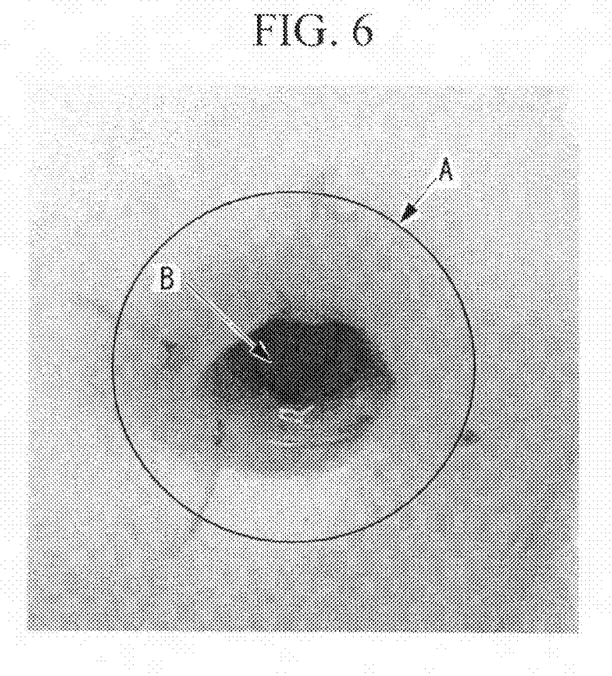
FIG. 6 shows a photograph of an engraftment condition of artificial cartilage tissue prepared by using a bovine serum in Example 2 of artificial cartilage tissue according to an embodiment of the present invention.

On the other hand, regarding the artificial cartilage tissue prepared using fetal bovine serum, engraftment was recognized in one out of the two samples. In the other sample, the center of the implanted site was greatly depressed, and disappearance of bone under the cartilage (subchondral bone) was recognized. The photograph is shown in FIG. 6. Here, the symbol A shows the implanted site, and the symbol B shows the depression due to the disappearance of subchondral bone. The causative factor of this disappearance of the subchondral bone is considered to be an antigen-antibody reaction between pig and a fetal bovine serum constituent contained in the artificial cartilage tissue. The list of the implanted artificial cartilage tissues and the results thereof are collectively shown in Table 2.

TABLE 2

| Sample No. | Serum Used | Water Retention mg $H_2O$/mg | Collagen Content μg/mg of dry weight | Collagen Content μg/mg of wet weight | Condition of Artificial Cartilage Tissue |
|---|---|---|---|---|---|
| 1 | Porcine | 11.4 | 212 | 17.1 | Engrafted |
| 2 | Porcine | 12.6 | 200 | 14.7 | Engrafted |
| 3 | Porcine | 12.2 | 176 | 13.3 | Engrafted |

TABLE 2-continued

| Sample No. | Serum Used | Water Retention mg $H_2O$/mg | Collagen Content µg/mg of dry weight | Collagen Content µg/mg of wet weight | Condition of Artificial Cartilage Tissue |
|---|---|---|---|---|---|
| 4 | Fetal bovine | 15.8 | 196 | 11.7 | Engrafted |
| 5 | Fetal bovine | 14.3 | 218 | 14.3 | Depression of subchondral bone |
| 6 | Porcine | 14.0 | 166 | 11.1 | Engrafted |

5. Conclusion

The result of implantation of artificial cartilage tissues prepared by using porcine serum into porcine articular cartilages showed that artificial cartilage tissues having a water retention of 11.4 mg $H_2O$/mg of dry weight to 14.0 mg $H_2O$/mg of dry weight, a collagen content per dry weight of 166 µg/mg to 212 µg/mg, and a collagen content per wet weight of 11.1 µg/mg to 17.1 µg/mg were engrafted. On the other hand, the result of implantation of artificial cartilage tissues prepared by using fetal bovine serum into porcine articular cartilages, showed that a large disappearance of the subchondral bone, considered to be caused by an antigen-antibody reaction, was recognized in 1 out of 2 samples.

Example 3

Transforming Growth Factor-β1 and Mechanical Strength

1. Purpose

The purpose is to ensure the effect of the transforming growth factor-β1 on the mechanical strength of an artificial cartilage tissue, and to discuss the concentration to be added into the medium.

2. Preparation of Artificial Cartilage Tissue

According to the method described in Example 1, artificial cartilage tissues were prepared using cells derived from porcine articular cartilage. In the preparation step using the silicon rings shown in FIG. 1A and FIG. 1B, media containing different concentrations of the transforming growth factor-β1 (TGF-β1) were used. The TGF-β1 concentration in the medium was 2.5, 5, 10, 20, and 40 ng/mL, each of which was referred to as the 2.5 ng/mL group, the 5 ng/mL group, the 10 ng/mL group, the 20 ng/mL group, and the 40 ng/mL group.

(3) Measurement of Tear Strength

According to the method described in Measurement Example 1 (1), the tear strength of the prepared porcine artificial cartilage tissue was measured. Two samples were used in the 2.5 ng/mL group and four samples were used in the other groups.

Figure 7:
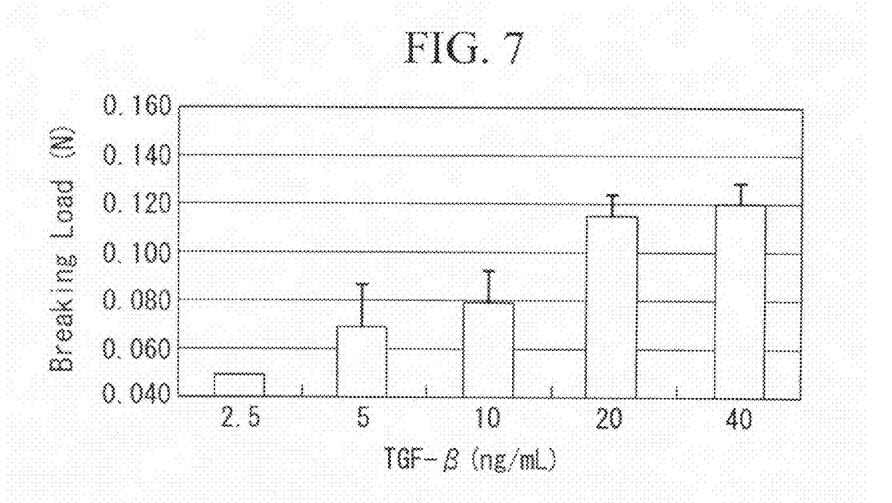
FIG. 7 is a graph showing the relation between concentration of transforming growth factor-β1 and tear strength in Example 3 of artificial cartilage tissue according to an embodiment of the present invention.

As a result, the tear strength was increased depending on the TGF-β1 concentration, and reached an approximately plateau level when the concentration was 20 ng/mL or more (FIG. 7). The upper limit of the TGF-β1 concentration is not specifically limited, and a person skilled in the art will appreciate that up to approximately 50 ng/mL concentration can be used (for example, refer to Blunk T, et al., Differential effect of growth factors on tissue-engineered cartilage. Tissue Engineering, 8, 73-84 (2002)).

4. Conclusion

It was shown that TGF-β1 is effective to improve the mechanical strength of artificial cartilage tissue, and the effect is maximized when the concentration in the medium is 20 ng/mL or more.

Example 4

Preparation of Artificial Cartilage Tissue Using Cells Derived from Human Articular Cartilage and its Mechanical and Biochemical Properties 1. Purpose The purpose is to prepare an artificial cartilage tissue using cells derived from human articular cartilage, to select the main constituents reflecting the mechanical strength, and to understand the contents of the main constituents in the artificial cartilage tissue, having the suturable mechanical strength.

2. Cell Isolation

Cartilages were collected from femoral heads extracted from four patients suffering from right femoral neck fracture (three females aged 78, 78, and 88, and a male aged 49) at the time of total hip arthroplasty. The collection of cartilage was performed under the approval of the patients and the ethics committee of the medical institution. Chondrocytes were isolated from the collected cartilage according to the method described in Example 1. However, human serum (Uniglobe Research Corporation) was used instead of porcine serum.

3. Monolayer Culture

The monolayer culture was performed as follows according to a partially modified method of Example 1. The isolated chondrocytes were suspended in 30 mL of a DMEM/F-12 medium containing 10 ng/mL bFGF, 100 ng/mL IGF-I, 10% human serum, 25 µg/mL L-ascorbic acid, and 10 µg/mL gentamycin, and then inoculated in a culture dish (Becton, Dickinson and Company.) having a diameter of 15 cm.

Then, the cells were cultured under a presence of 5% $CO_2$ at 37° C. for 16 days to keep the necessary number of cells ($2.1 \times 10^7$) for the next step. The medium was replaced every 3 to 4 days.

4. Three Dimensional Culture

A DMEM/F-12 medium containing 0.2% pronase and 10 µg/mL gentamycin was added to the culture dish containing the monolayer cultured chondrocytes, which was treated under the presence of 5% $CO_2$ at 37° C. for 15 minutes. The medium containing detached cells was collected and centrifuged at 300×g. The supernatant was disposed. The precipitation was digested by adding a medium containing 0.025% collagenase-P under the presence of 5% $CO_2$ at 37° C. for 1 hour. The dispersed cells were suspended in a physiological saline solution containing 1.2% sodium alginate with a density of $2 \times 10^6$/mL. Hereinafter, according to a partially modified method of Example 1, three dimensional culture was performed using an alginate gel.

The sodium alginate solution having the suspended cells was placed in a 50 mL disposable syringe, and a 22G injection needle was equipped therein. The plunger of the syringe was pushed in, and the content liquid was added dropwise to a 102 mmol/L $CaCl_2$ solution. 10 minutes after the dropwise addition, the beads were washed with a physiological saline solution three times. Then, the cells were cultured in a DMEM/F-12 medium containing 100 ng/mL IGF-I, 100 ng/mL bone morphogenetic protein (BMP)-7 (R&D Systems), 5% or 10% human serum, 25 µg/mL L-ascorbic acid, and 10 µg/mL gentamycin under the presence of 5% $CO_2$ at 37° C. for 24 days. The liquid volume of the medium was 40 mL, and a culture dish having a diameter of 15 cm was used. The medium was replaced every three days.

5. Formation of Artificial Cartilage Tissue

After 24 days of three dimensional culture, according to the method described in Example 1, 55 mmol/L sodium citrate buffer (pH 6.8) containing 0.15 mol/L sodium chloride was added at a 5-to-1 volume ratio to the alginate beads, to dissolve the gelled alginic acid. The obtained suspension was centrifuged at 300×g at 4° C. for 5 minutes, and then a physiological saline solution was added to the precipitation, which was stirred and centrifuged in the same manner. This process was repeated once more using a physiological saline solution, and was repeated once using a medium described below. The chondrocytes having cartilage matrix were collected as a precipitate.

About 250 µL of the precipitate containing chondrocytes was suspended in a DMEM/F-12 medium containing 5 or 20 ng/mL TGF-β1, 100 ng/mL IGF-I, 100 ng/mL BMP-7, 5%, 10%, or 15% human serum, 25 µg/mL L-ascorbic acid, and 10 µg/mL gentamycin. Next, the cell suspension was gently placed in the container shown in FIG. 1A and FIG. 1B, and left under the presence of 5% $CO_2$ at 37° C. for 16 hours, to allow a precipitate of cells with a cartilage matrix in the silicon ring. The top layer of the silicon ring was taken out. Next, 10 mL of the medium used for the suspension of cells was added to soak the cells precipitated in the silicon ring of the bottom layer. In this condition, the cells were cultured under the presence of 5% $CO_2$ at 37° C. for 21 days.

The diameter of the artificial cartilage tissue prepared according to the above method was about 13 mm and the thickness thereof was about 1 mm. 29 samples were selected. Disc-shaped samples having a diameter of 5 mm were punched out, and the tear strength was measured. Moreover, after the disc-shaped samples were punched out, the remaining samples were used to measure the water retention, the collagen content, and the proteoglycan content.

6. Correlation of Tear Strength and Content of Main Constituents

The results of correlation analysis between tear strength and water retention, collagen content, or proteoglycan content are shown in Table 3.

TABLE 3

| Main Constituent Content | | Correlation with Breaking Load |
|---|---|---|
| Water Retention | | r = −0.794 (p < 0.01) |
| Collagen Content | per wet weight | r = 0.826 (p < 0.01) |
|  | per dry weight | r = 0.821 (p < 0.01) |
| Proteoglycan Content | per wet weight | r = 0.703 (p < 0.01) |
|  | per dry weight | r = −0.301 (NS) | r: Correlation Coefficient
NS: Not Significant

The most correlated measurement item with tear strength was collagen content per wet weight, followed by collagen content per dry weight and water retention in this order. The proteoglycan content per wet weight was also significantly correlated, however the proteoglycan content per dry weight was not correlated.

Figure 8:
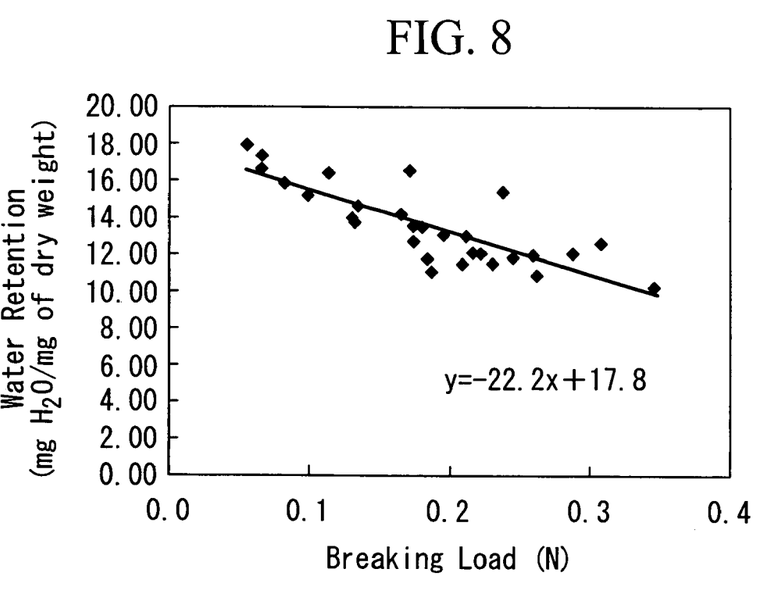
FIG. 8 is a graph showing the relation between water retention and tear strength in Example 4 of human artificial cartilage tissue according to an embodiment of the present invention.
Figure 9:
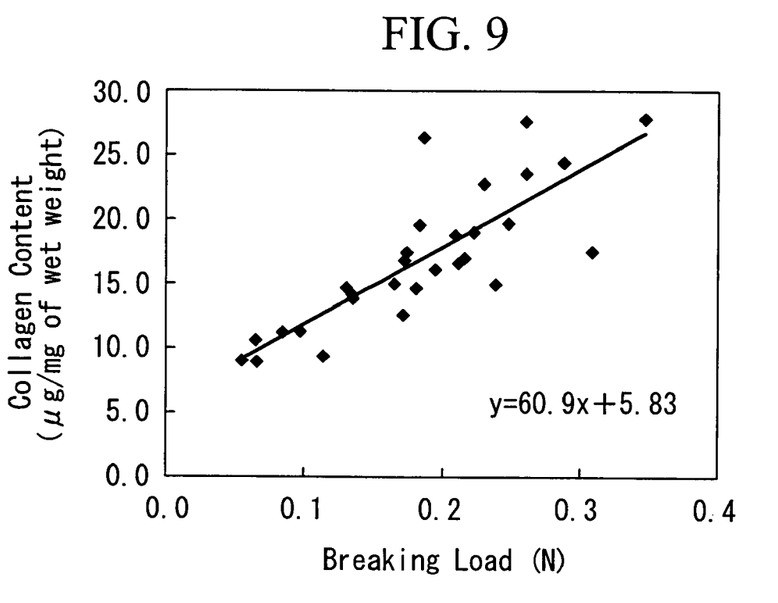
FIG. 9 is a graph showing the relation between collagen content and tear strength in Example 4 of human artificial cartilage tissue according to an embodiment of the present invention.
Figure 10:
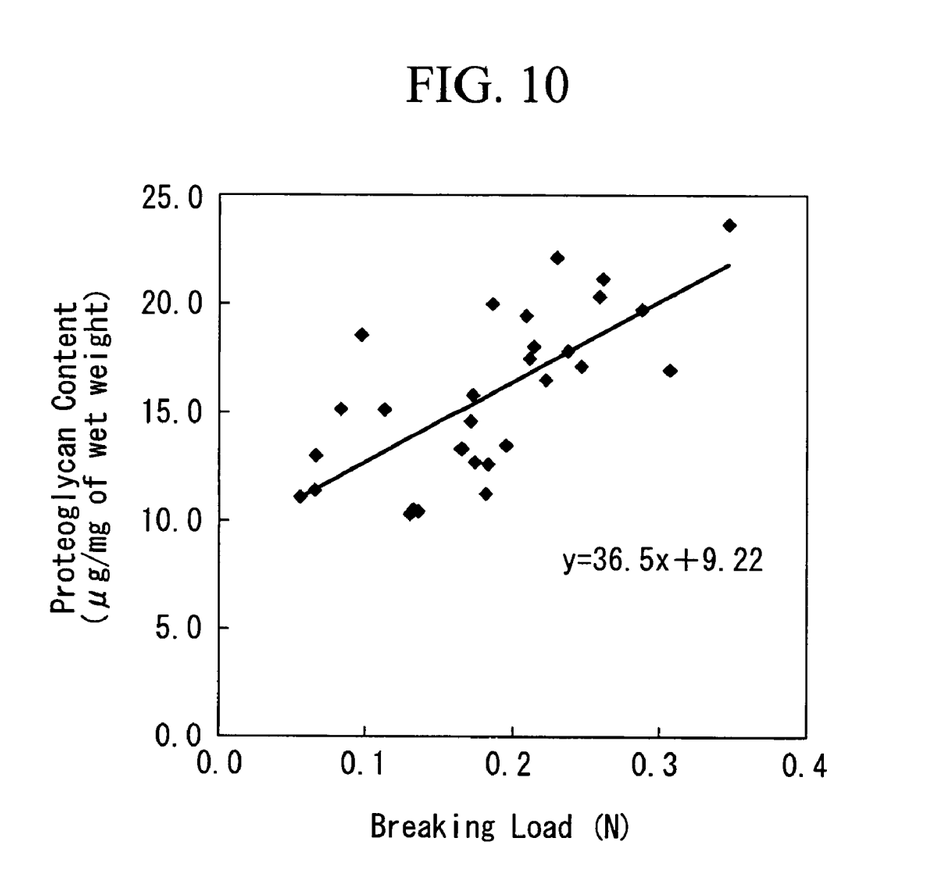
FIG. 10 is a graph showing the relation between proteoglycan content and tear strength in Example 4 of human artificial cartilage tissue according to an embodiment of the present invention.

Moreover, FIG. 8 shows the correlation between water retention and tear strength, FIG. 9 shows the correlation between collagen content per wet weight and tear strength, and FIG. 10 shows the correlation between proteoglycan content per wet weight and tear strength. According to these figures, the correlation equation between water retention and tear strength (breaking load) is: water retention (mg $H_2O$/mg of dry weight)≈−22.2×breaking load+17.8, the correlation equation between collagen content and tear strength is: collagen content (µg/mg of wet weight)≈60.9×breaking load+5.83, and the correlation equation between proteoglycan content and tear strength is: proteoglycan content (µg/mg of wet weight)≈36.5×breaking load+9.22.

The water retention of artificial cartilage tissue having a tear strength more than 0, that is, a suturable strength with a 6-0 nylon thread, was about 17.8 mg $H_2O$/mg of dry weight or less, the collagen content thereof was about 5.83 µg/mg of wet weight or more, and the proteoglycan content was about 9.22 µg/mg of wet weight or more.

7. Conclusion

The human artificial cartilage tissue having a suturable strength had at least a water retention of about 17.8 mg $H_2O$/mg of dry weight or less, a collagen content of about 5.83 µg/mg of wet weight or more, or a proteoglycan content of about 9.22 µg/mg of wet weight or more.

Example 5

Implantation of Artificial Cartilage Tissue Prepared by Using Cells Derived from Porcine Articular Cartilage and Autologous Serum into Pig Knee Joint 1. Purpose The purpose is to select measurement items reflecting the engraftment result of the artificial cartilage tissue and to understand the range thereof.

2. Collection of Cartilage and Blood

Five approximately 6 month old female pigs (hybrid of duroc father and cotswold mother) were used. The body weight at the time of usage was 90.6 to 105.0 kg. As a preanesthetic medication, 0.05 mg/kg of atropine sulfate (Tanabe Seiyaku Co., Ltd.) was intramuscularly administrated. Then, 20 mg/kg of ketamine hydrochloride (Sankyo Co., Ltd.) were intramuscularly administrated to effect anesthesia. Next, the pigs were placed on an operating table and subject to inhalation anesthesia with isoflurane (Dainippon Sumitomo Pharma Co., Ltd.).

The vicinity of the knee of the left hind leg was shaved off, and the target site was disinfected with Isodine (Meiji Seika Kaisha, Ltd.) and 70% ethanol. Next, the skin, the muscular layer, and the articular capsule were incised to expose the medial condyle of femur. The non-weight-bearing region of the articular surface was marked at 2 or 3 points using a trephine having a diameter of 8 mm, and the cartilage in these points was collected. Moreover, about 1 L of blood was collected from the external jugular vein, from which serum was isolated.

3. Artificial Cartilage Tissue

According to the method described in Example 1, the artificial cartilage tissue was prepared by using the obtained cartilage and serum. The autologous serum concentration was 5%, the bFGF concentration was 30 ng/mL, the TGF-β1 concentration was 20 ng/mL, and the TGF-β2 concentration was 100 ng/mL. About 2.5 months was required for the preparation.

The diameter of the prepared artificial cartilage tissue was about 14 mm and the thickness thereof was about 1 mm. These samples were punched out in a disc-shape having a diameter of 8 mm, and the obtained samples were used for implantation. After the disc-shaped samples were punched out, the remaining samples were used to measure the water retention, the DNA content, the collagen content, the proteoglycan content, and the tear strength.

4. Implantation into Experimental Animal

The pigs were anesthetized similarly to the manner when the cartilage and blood were collected. The vicinity of the knee of the right hind leg was shaved off, and sufficiently disinfected with Isodine (Meiji Seika Kaisha, Ltd.) and 70% ethanol. Next, the skin, the muscular layer, and the articular capsule were incised to expose the medial condyle of the femur. One cartilage full-thickness defect having a diameter of 8.25 mm was formed in the weight-bearing region of the articular surface, and the artificial cartilage tissue prepared by using the cartilage and serum derived from the same individual was inserted into the defect. Next, using a 6-0 nylon suture thread (Matsuda Ika Kogyo, Co., Ltd.), the artificial cartilage tissue was sutured to the cartilage around the implanted site at 4 points. The inside of the joint cavity was sufficiently washed with a physiological saline solution (Otsuka Pharmaceutical Co., Ltd.), and then the articular capsule, the muscular layer, and the skin were sequentially sutured. After the implantation operation, the pigs were kept warm until they woke up from anesthesia. On the day of the implantation operation and everyday for 7 days after the operation, 0.05 mg/kg of dihydrostreptomycin sulfate (Meiji Seika Kaisha, Ltd.) was intramuscularly administrated.

5. Anatomy and Observation of Implanted Tissue

On the 26th week after implantation of the artificial cartilage tissue, the pigs were anesthetized with pentobarbital (Dainippon Pharmaceutical Company Limited.), and then allowed to bleed to death from the carotid artery. The condyle of femur of the right hind leg was separated, and the condition of the implanted site was macroscopically observed. As a result, engraftment was ensured for all implanted artificial cartilage tissues. However, irregularity was found in the implanted sites of some examples. Next, the cartilage of the implanted site was collected using a trephine having a diameter of 3 mm, and the proteoglycan content was measured. Then, the femur was fixed with a 15% neutral buffered formalin solution containing 1% CPC, and cut out while avoiding the site where the cartilage was collected. Thereafter, according to the usual method, the femur was decalcified, embedded in paraffin, sliced, and stained with safranin-O/fast green. According to ICRS score (J. Bone Joint Surg. Org., 2003, 85-A, 45-57) or Wakitani's score (J. Bone Joint Surg. Am., 1994, 76, 579-92), the implanted site of the tissue preparation was evaluated under blind, and correlations between the implanted cultured cartilage tissue and the respective measurement items were discussed. Higher rate of ICRS score and lower rate of Wakitani's score mean better engraftment.

Moreover, since the proteoglycan content in cartilage is a good index to reflect the degree of disability of cartilage (Hamerman D.: Orthop. Rev., 1988, 17, 353-360), the correlations between proteoglycan content in the cartilage implanted site and the respective measurement items of the implanted cultured cartilage tissue were also discussed.

6. Result

The correlation coefficients and the assay results are shown in Table 4. Each measurement item of the artificial cartilage tissue used for implantation is referred to as "measurement item".

TABLE 4

| Evaluation Index | "Water Retention" | "DNA content" dry weight | "DNA content" wet weight | "Collagen Content" dry weight | "Collagen Content" wet weight |
|---|---|---|---|---|---|
| ICRS | −0.851 (NS) | −0.851 (NS) | −0.076 (NS) | 0.449 (NS) | 0.625 (NS) |
| Wakitani | 0.843 (NS) | 0.874 (NS) | 0.133 (NS) | −0.411 (NS) | −0.598 (NS) |
| Proteoglycan Content | −0.916 (p < 0.05) | −0.632 (NS) | 0.325 (NS) | 0.885 (p < 0.05) | 0.952 (p < 0.05) |

| Evaluation index | "Proteoglycan Content" dry weight | "Proteoglycan Content" wet weight | "Tear Strength" |
|---|---|---|---|
| ICRS | 0.850 (NS) | 0.808 (NS) | 0.525 (NS) |
| Wakitani | −0.871 (NS) | −0.813 (NS) | −0.524 (NS) |
| Proteoglycan Content | 0.707 (NS) | 0.908 (p < 0.05) | 0.923 (p < 0.05) |

The upper row shows correlation coefficients and the lower row shows assessment results.

Although no measurement item which significantly correlates with the ICRS score or Wakitani's score was recognized, the correlation coefficient was 0.8 or more regarding "proteoglycan content" per dry weight or per wet weight. Moreover, the correlation coefficient was also 0.8 or more regarding "water retention".

On the other hand, the proteoglycan content in the implanted site was positively and significantly correlated with "collagen content", "proteoglycan content" (only per wet weight), and "tear strength" of the implanted artificial cartilage tissue, and was negatively and significantly correlated with "water retention" thereof. Moreover, regarding the correlation with "collagen content" and "proteoglycan content", the correlation coefficient per wet weight was higher than the coefficient per dry weight.

7. Conclusion 1A higher level of "collagen content", "proteoglycan content", "tear strength" and a lower level of "water retention" of the implanted artificial cartilage tissue showed better engraftment. Regarding the "collagen content" and "proteoglycan content", the results per wet weight showed better engraftment compared to the results per dry weight.

Moreover, regarding the artificial cartilage tissue used in the present Example, the maximum value of "water retention" and the minimum values of "collagen content" and "proteoglycan content" are shown in Table 5. In the present Example, engraftment of the implanted artificial cartilage tissue was recognized in all individuals. Therefore, it is shown that engraftment was successful as long as the artificial cartilage had a value of "water retention" shown in Table 6 or lower, and values of "collagen content" and "proteoglycan content" shown in Table 6 or higher.

TABLE 5

| Water Retention Maximum Value mg $H_2O$/mg of dry weight | Collagen Content Minimum Value μg/mg of wet weight | Proteoglycan Content Minimum Value μg/mg of wet weight |
|---|---|---|
| 16.00 | 12.4 | 12.2 |

From the results obtained in Examples 1, 2, 4, and 5, respective measurement values capable of retaining the suturability and the engraftability, are collectively shown in Table 6.

TABLE 6

| Example | Species | Performance | Water Retention mg H2O/mg of dry weight | Collagen Content µg/mg of wet weight | Proteoglycan Content µg/mg of wet weight |
|---|---|---|---|---|---|
| 1 | Porcine | Stichability | 16.0 or less | 5.57 or more | 13.4 or more |
| 2 | Porcine | Engraftability | 14.0 or less | 11.1 or more | Not measured |
| 4 | Human | Stichability | 17.8 or less | 5.83 or more | 9.22 or more |
| 5 | Porcine | Engraftability | 16.0 or less | 12.4 or more | 12.2 or more |

What is claimed is:

1. An artificial cartilage tissue to which no bovine serum or plasma has been added and which does not contain an exogenous scaffold derived from non-cartilage-derived cells, but contains mammalian cartilage-derived cells and an extracellular matrix formed by the cartilage-derived cells, and has at least one of the following properties (1), (2), and (3):
(1) a water retention per mg of tissue dry weight of 17.8 mg or less;
(2) collagen of 5.57 µg or more per mg of tissue wet weight is contained; and
(3) proteoglycan of 9.22 µg or more per mg of tissue wet weight is contained, wherein the mammalian cartilage-derived cells are only those obtained by culturing under the presence of serum or plasma derived from a mammal of the same species, wherein,
the artificial cartilage tissue is obtained by culturing in a medium containing a growth factor belonging to the transforming growth factor-β superfamily.

2. The artificial cartilage tissue according to claim 1, wherein the serum or plasma is derived from a mammal over 6 months old.

3. The artificial cartilage tissue according to claim 1, wherein the serum or plasma is derived from the same individual.

4. The artificial cartilage tissue according to claim 1, wherein the mammal is a human.

5. The artificial cartilage tissue according to claim 1, wherein the medium contains ng/mL or more of the growth factor belonging to the transforming growth factor-β superfamily.

6. The artificial cartilage tissue according to claim 1, wherein the artificial cartilage tissue has a disc-shape.

7. The artificial cartilage tissue according to claim 1, wherein the artificial cartilage tissue has at least one of the following properties (4), (5), and (6):
(4) a thickness is about 1 mm;
(5) a diameter is between 5 mm and 14 mm; and
(6) a sum of thickness and diameter is 15 mm or less.

8. The artificial cartilage tissue according to claim 1, wherein the artificial cartilage tissue is configured to be sutured to a target site.

* * * * *